(12) United States Patent
Weber et al.

(10) Patent No.: US 8,049,007 B2
(45) Date of Patent: *Nov. 1, 2011

(54) PREPARATION OF AMOROLFINE

(75) Inventors: Beat Weber, Zofingen (CH); Stefan Rosenberger, Zofingen (CH)

(73) Assignee: Galderma S.A., Cham (CH)

( * ) Notice: Subject to any disclaimer, the term of this patent is extended or adjusted under 35 U.S.C. 154(b) by 240 days.

This patent is subject to a terminal disclaimer.

(21) Appl. No.: 12/457,789

(22) Filed: Jun. 22, 2009

(65) Prior Publication Data

US 2010/0004442 A1 Jan. 7, 2010

Related U.S. Application Data

(63) Continuation of application No. PCT/EP2007/064493, filed on Dec. 21, 2007.

(30) Foreign Application Priority Data

Dec. 21, 2006 (EP) .................... 06126867

(51) Int. Cl.
 *C07D 265/30* (2006.01)
(52) U.S. Cl. ....................................... 544/106
(58) Field of Classification Search ................... 544/106
 See application file for complete search history.

(56) References Cited

U.S. PATENT DOCUMENTS 7,795,425 B2 * 9/2010 Weber et al. .................. 544/106

* cited by examiner

*Primary Examiner* — Golam M Shameem

(74) *Attorney, Agent, or Firm* — Buchanan Ingersoll & Rooney, P.C.

(57) ABSTRACT

Amorolfine base, which is a compound of formula (I):

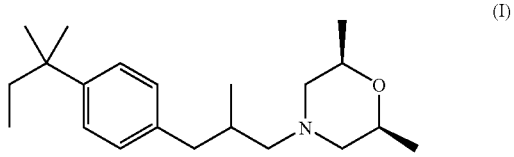

is improvedly prepared by:
 (i) contacting a compound of formula (II):

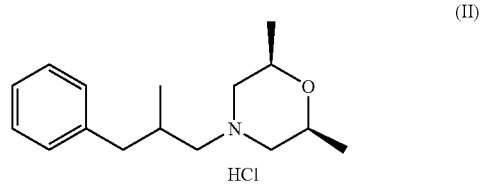

with a Friedel-Crafts catalyst; and
 (ii) adding one equivalent of 2-halogeno-2-methylbutane, wherein the reaction mixture obtained in step (i) is cooled to a temperature from −40° to −60° C. prior to step (ii) and the Friedel-Craft catalyst is selected from the group consisting of gallium chloride, antimony pentafluoride, molybdenum pentachloride, indium chloride, antimony pentachloride.

7 Claims, No Drawings

PREPARATION OF AMOROLFINE

CROSS-REFERENCE TO PRIORITY/PCT APPLICATIONS

This application claims priority under 35 U.S.C. §119 of EP 06126867.8, filed Dec. 21, 2006, and is a continuation/national phase of PCT/EP 2007/064493, filed Dec. 21, 2007 and designating the United States (published in the English language on Jun. 26, 2008 as WO 2008/074887 A1), each hereby expressly incorporated by reference in its entirety and each assigned to the assignee hereof.

BACKGROUND OF THE INVENTION

1. Technical Field of the Invention

The present invention relates to an improved process for the preparation of Amorolfine base, which is an intermediate used in the production of Amorolfine (AMF) hydrochloride (Amorolfine HCl).

2. Description of Background and/or Related and/or Prior Art

Amorolfine HCl is an active pharmaceutical ingredient (API) formulated into topical anti-mycotic (antifungal) compositions.

FR 2,463,767 describes methods of producing Amorolfine HCl and intermediates in such production. In particular, a method for the production of Amorolfine base (AMF base), which is a compound of formula (I):

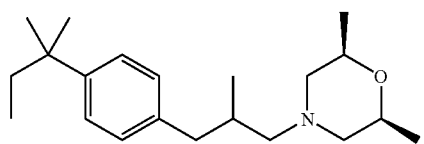
(I)

is described, the method involving the step of reacting a compound of the formula (a):

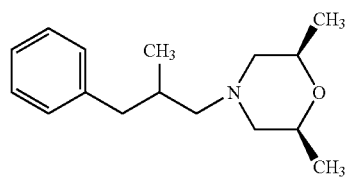
(a)

with a compound of the formula (b):

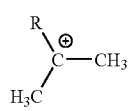
(b)

in a Friedel-Crafts alkylation to form AMF base. The suggested catalysts are those known for use as Friedel-Crafts catalysts, such as aluminum chloride, iron chloride, zinc chloride, boron trifluoride, hydrogen fluoride, sulfuric acid, and phosphoric acid. Sulfuric acid is stated to be the preferred catalyst. To provide a compound of the formula (b):

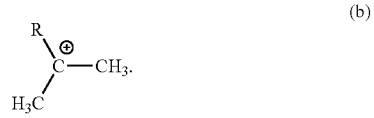
(b)

FR 2,463,767 suggests using tertiary alcohols such as 2-methyl-2-butanol, or tertiary chlorides such as 2-chloro-2-methylbutane. However, only 2-methyl-2-butanol is exemplified. The reaction temperature is noted as not being of critical importance but is suggested to be, in general, from 0° to 50° C., preferably from 18° to 20° C.

On another side, it is generally known that Friedel-Crafts catalysts show different activities in the alkylation reaction of aromatic compounds. As disclosed in the "KIRK-OTHMER Encyclopedia of Chemical Technology", $4^{th}$ Edition, Vol. 11, 1994, page 1071 (Table 1), more active is the Friedel-Crafts catalyst, more expected are side reactions.

There remains a need for improved processes for the production of Amorolfine salts, for example Amorolfine HCl, and its intermediates, such as Amorolfine base.

SUMMARY OF THE INVENTION

It has now been discovered that significant benefits can be obtained if a tertiary chloride such as 2-chloro-2-methylbutane is added to a compound of the formula (a):

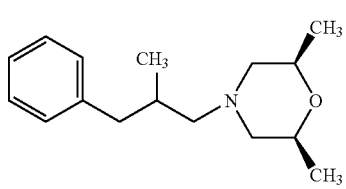
(a)

in mixture with a Friedel-Craft catalyst selected from the group consisting of gallium chloride, antimony pentafluoride, molybdenum pentachloride, indium chloride, antimony pentachloride at a temperature from −40° to −60° C., preferably around −50° C.

The present invention this provides an improved method of producing Amorolfine base, with a higher yield and lower impurity assay resulting.

DETAILED DESCRIPTION OF BEST MODE AND SPECIFIC/PREFERRED EMBODIMENTS OF THE INVENTION

According to a first embodiment of the invention, there is provided a process of preparing a compound of formula (I):

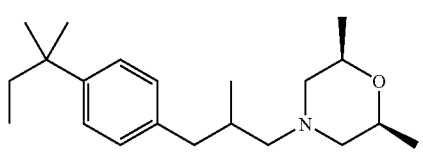
(I)

said process comprising the steps of:
(i) contacting a compound of formula (II):

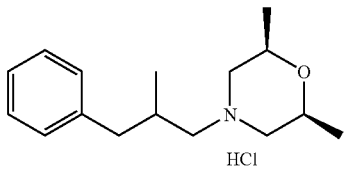
(II)

with a Friedel-Crafts catalyst selected from the group consisting of gallium chloride, antimony pentafluoride, molybdenum pentachloride, indium chloride, antimony pentachloride, preferably at a temperature in the range of 20° to 30° C.; and (ii) adding one equivalent of 2-halogeno-2-methylbutane, taking into account that the reaction mixture obtained in step (i) is cooled to a temperature from −40° to −60° C. prior to step (ii) (addition of the 2-halogeno-2-methylbutane).

Among the Friedel-Crafts catalysts used, gallium and antimony catalysts are preferred.

As used herein the term "Amorolfine base" (AMF base) refers to compounds of formula (I) and the term "bepromoline HCl" refers to compounds of formula (II).

As used herein the term "2-halogeno-2-methylbutane" refers to 2-methylbutane substituted in position 2 by an halogen atom selected from the group consisting of bromine, chlorine, iodine and fluorine.

More preferably, the halogen is chlorine and consequently the 2-halogeno-2-methylbutane is 2-chloro-2-methylbutane.

The reaction mixture obtained in step (i) may typically be cooled to a temperature from −40° to −60° C., generally −50° C., prior to step (ii), i.e., addition of the 2-halogeno-2-methylbutane.

Friedel-Crafts catalyst is generally used in dichloromethane (DCM).

Moreover, the compound of formula (II) is generally present in 1 part of 2-halogeno-2-methylbutane per 1 part compound of formula (II).

As used herein, the term "part" refers to a number of moles.

In one embodiment, the process of producing a compound of formula (I) includes, after steps (i) and (ii) above, one or more of the following steps (preferably performed successively):

(a) pouring the reaction mixture from step (ii) onto an ice-water mixture;
(b) separating the organic phase (i.e., DCM);
(c) washing the organic phase with optionally acidified, water,
(d) washing the organic phase with water;
(e) washing the organic phase from step (d) with a solution of sodium hydroxide;
(f washing the organic phase from step (e) with water;
(g) exchanging the dichloromethane solvent to toluene;
(h) performing toluene/water extractions;
(i) removing the toluene by distillation; and
(j) distilling the crude Amorolfine base from step (i).

As the preferred 2-halogeno-2-methylbutane is 2-chloro-2-methylbutane according to present invention, there is provided the preferred process of producing a compound of formula (I):

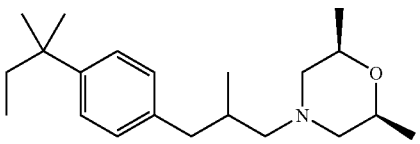
(I)

said process comprising the steps of:
(i) contacting a compound of formula (II):

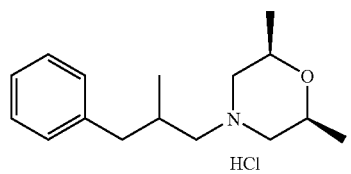
(II)

with a Friedel-Crafts catalyst selected from the group consisting of gallium chloride, antimony pentafluoride, molybdenum pentachloride, indium chloride, antimony pentachloride, at a temperature in the range of 20 to 30° C.; and (ii) adding 2-chloro-2-methylbutane,
taking into account that the reaction mixture obtained in step (i) is cooled to a temperature from −40° to −60° C. prior to step (ii) (addition of the 2-chloro-2-methylbutane).

This process can be performed as described above and can comprise one or more of the steps (a) to (j) above.

According to the present invention, the process of producing a compound of formula (I):

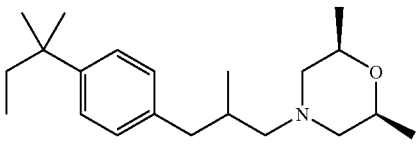
(I)

comprises steps (i) and (ii). Said steps can be preceded by the step of contacting a compound of the formula (III):

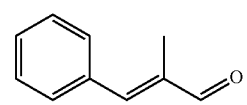
(III)

with a compound of formula (IV):

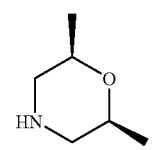
(IV)

in the presence of a catalyst such as palladium precipitated onto carbon, methanol and hydrogen gas, wherein the step of contacting the compound of the formula (III) with the compound of formula (IV) is optionally conducted under basic conditions, with acetic acid added once the consumption of the hydrogen gas has ceased.

Compounds of formulae (III) and (IV) are termed herein "α-methylcinnamaldehyde" and "cis-2,6-dimethyl morpholine" (DMM), respectively.

The basic conditions are generally provided by KOH, typically, 1.8 mol-% KOH.

According to a second embodiment of the present invention, there is provided a process of producing a compound of formula (V):

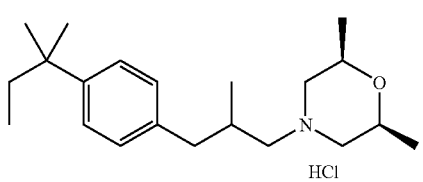

(V)

comprising a process as described above for the first embodiment of the present invention.

This compound of formula (V) can be obtained from Amorolfine base (compound (I)) by virtue of a salification step.

Typical and usual features of each embodiment of the invention are as for each of the other embodiments of the invention mutatis mutandis.

Throughout the specification, unless the context demands otherwise, the terms "comprise" or "include", or variations such as "comprising" and "including" will be understood to imply the inclusion of a stated feature, or group of features, but not to the exclusion of any other feature, or group of features.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Production of Bepromoline HCl

General Considerations:

A mixture of 1 part of α-methyl-cinnamaldehyde to one part of cis-2,6-dimethyl-morpholine (DMM) is hydrogenated in methanol in the presence of catalytic amount of palladium on carbon optionally under basic conditions until the uptake of $H_2$ gas ceases, this indicating completion of the reduction of the C=C double bond. Acetic acid is then added for the reduction of the C=N double bond under hydrogen pressure; the C=N double bond is formed from the aldehyde and the amino moiety of the two reactants, α-methyl-cinnamaldehyde and DMM, respectively.

The catalyst is then filtered off and the methanol is removed by distillation. Toluene is added and the inorganic components are removed by washing with water. Toluene and unreacted DMM are distilled off. Then fresh toluene is added and HCl gas is bubbled through the solution. The pH is adjusted to 3-4. The bepromoline HCl is centrifuged and dried.

Schematic of Production of Bepromoline HCl:

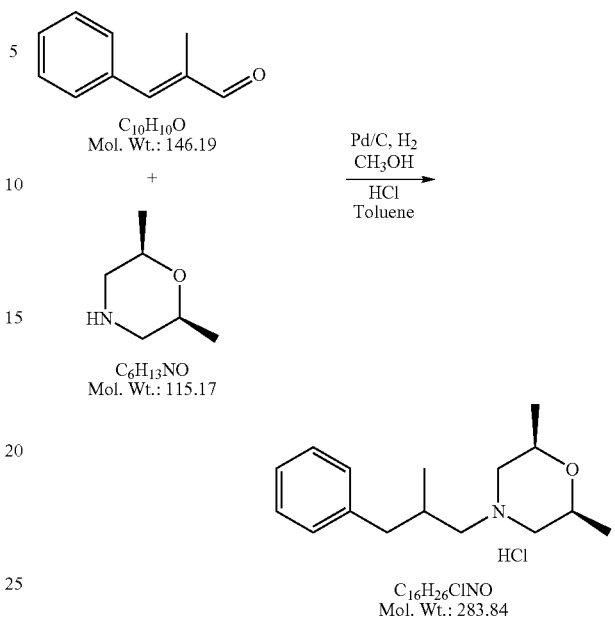

Provision of Basic Conditions:

Basic conditions were provided by KOH, which is used to neutralize the acidic components present in the α-methyl-cinnamaldehyde. The absence of traces of acid improved the kinetic of the reaction. The reduction of the aldehyde function to the corresponding alcohol is avoided by addition of KOH.

Solvent:

Methanol might be substituted by toluene to avoid the later solvent exchange step.

Temperature of Hydrogenation:

40° C. is the optimum temperature for both hydrogenation steps. However, the temperature may typically be set at no more than 45° C., preferably from 30° to 45° C.

Acetic Acid:

The reduction of the C=N double bond formed from the aldehyde and the amino function of the two components is conducted under hydrogen pressure in acidic conditions after the addition of acetic acid.

A molar ratio of acetic acid to KOH is around 1.3 (+10%).

The acetic acid is typically added at a temperature range of from 40° to 45° C., and no more than 45° C.

Toluene Exchange:

The toluene is advantageously added to facilitate the phase separations and the distillation step of the un-reacted DMM, thus improving the purity of bepromoline.

Bepromoline.HCl Purity:

The trans isomers (VI) and (VII) of bepromoline, coming from trans isomers presents as by products in the 2,6-dimethyl morpholine starting material, are partially eliminated during the crystallization of bepromoline HCl.

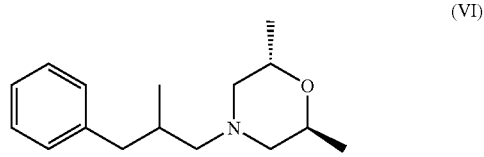

(VI)

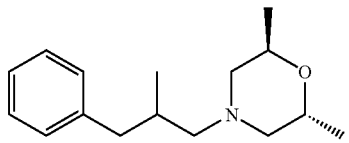

(VII)

The purity of the bepromoline HCl (cis isomer) is superior or equal to 99.5%.

Stability Temperature:

The product is stable up to 150° C.

b) Synthesis:

(Weights are given for 1 kmol α-methyl-cinnamaldehyde).

A reactor was charged with 146 kg α-methyl-cinnamaldehyde, 115 kg cis-2,6-dimethyl-morpholine, 2.1 kg 50% KOH, 278 kg methanol and 5.8 kg of a palladium/carbon catalyst and then filled with hydrogen at 15-25° C.

The hydrogenation was then run at a pressure of ~2 bar and 35-45° C. until $H_2$ consumption ceased.

1.5 kg acetic acid was then added, and the hydrogenation was re-commenced. The hydrogenation was conducted at a pressure of ~2 bar and at a temperature of 40°-45° C. until no further $H_2$ was consumed.

The reaction mixture was filtered and the catalyst washed with methanol and purified water.

The solvents were distilled of at a temperature of up to 95° C. under vacuum.

Two extractions were performed using toluene and water. The waste water was drained off.

The solvent was then distilled off under vacuum.

The reactor was charged with 904 kg toluene and 33 kg HCl gas at a temperature of up to 50° C. Then the pH was adjusted to 3-4. The reaction mixture was cooled and then stored under agitation sufficiently to reached complete crystallization.

The mixture was centrifuged and washed with cold (0°-5° C.) toluene. A second crop of Bepromoline HCl was isolated from the mother liquor.

The process yielded 287 kg wet bepromoline HCl, which was then dried at 60° C. under vacuum. After drying, the first crop of Bepromoline HCl was 227 kg and the second 18 kg. This corresponds to a yield of 87%. (80% for the first crop Bepromoline HCl and 7% for the second crop).

EXAMPLE 2

Production of Amorolfine Base a) General Considerations:

1 part of bepromoline.HCl is treated with appropriate amount of gallium chloride in dichloromethane at room temperature. The resulting slurry is cooled to approximately –50° C., whereupon 1 to 1.1 parts of 2-chloro-2-methylbutane is added.

After an appropriate reaction time of around 2.5 hours, the reaction mixture is poured onto an ice-water mixture. The organic phase is separated and washed with acidic water, and then with sodium hydroxide solution. After a stripping with toluene, extractions with water are performed. The solvent is then removed. Then the residue is distilled.

Other Friedel-Craft catalyst selected among the group consisting of antimony pentafluoride, molybdenum pentachloride, indium chloride and antimony pentachloride can also be used instead of gallium chloride.

Reaction Temperature for the Addition of Friedel-Craft Catalyst to Bepromoline HCl:

The addition of Friedel-Craft catalyst to Bepromoline HCl takes place at room temperature. At lower temperatures the subsequent Friedel-Crafts alkylation fails partially or completely (Table 1).

TABLE 1

| Temperature (° C.) | Bepromoline assay in the crude Amorolfine base(%) |
| --- | --- |
| 20-30 | 8-14 |
| 0 | 14 |
| –20 | 100 |

Reaction Temperature for Friedel-Crafts Alkylation:

To decrease the fenpropimorph (FPM) by-product, the reaction is conducted at low temperature, preferably –50° C. (see Table 2):

TABLE 2

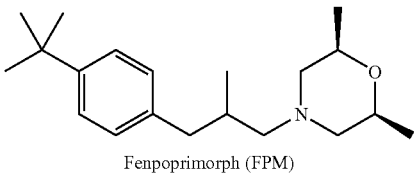

Fenpoprimorph (FPM)

| Temperature (° C.) | FPM (%) |
| --- | --- |
| –52 to –49 | 0.14-0.25 |
| –40 | 1.7 |
| –35 | 2.0 |
| –20 | 2.7 |

Fenpropimorph (FPM) is a problematic by-product as it is difficult to remove from the end product.

Ratio of Bepromoline HCl to 2-chloro-2-methylbutane:

Batches were performed with 10% excess 2-chloro-2-methylbutane and at a 1:1 ratio. The FPM assay is lower for the 1:1 ratio and thus this proportion is preferred.

Solvent Exchange:

Advantages result if the solvents are exchanged (i.e., toluene in place of DCM): the volume is reduced and the wastewater is contaminated with less chlorinated solvent.

Toluene-Water Extraction:

Those extractions are necessary to get the appropriate quality for the subsequent distillation. If these extractions are omitted, the Amorolfine base slightly decomposes at 180° C. The distillation becomes very sluggish and fumes are formed. The vacuum distillation is then not possible at plant scale.

The yield was approximately 90% of crude Amorolfine base.

b) Synthesis:

(Weights are Given for 1 kmol Bepromoline HCl)

The reactor was charged with an appropriate quantity of gallium chloride catalyst and 757 kg DCM. 284 kg bepromoline HCl in 946 kg DCM were added to the reactor at 20°-30° C. The reaction mixture was completed with 213 kg DCM and cooled to –50° C. 107 kg 2-chloro-2-methylbutane in 107 kg DCM were added at –50° C., although a temperature of –60° to –45° C. is acceptable, and stirred for 2.5 hours. Hydrolysis was performed using 255 kg ice and 785 kg water.

Phase Separation was then Performed.

Extractions using slightly acidic water (water and diluted HCl) were performed. A subsequent extraction was conducted using NaOH diluted in water to a pH>13. At a lower pH value there is incomplete HCl removal, leading to distillation problems. Two washes were performed with water.

Toluene was added and four water extractions were performed. Finally the solvent was distilled off under vacuum yielding crude Amorolfine base.

EXAMPLE 3

Distillation of Amorolfine Base a) General Considerations:

The distillation step is necessary to purify Amorolfine Base.

Schematic of the Distillation Process:

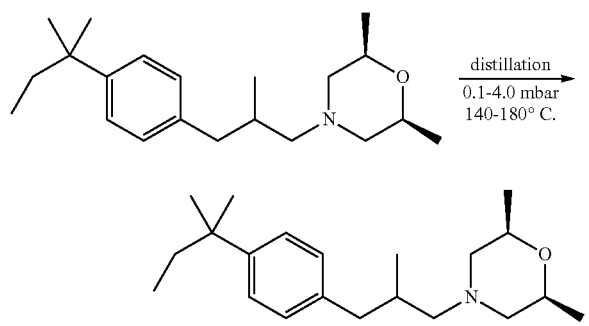

b) Distillation:

283 kg of crude Amorolfine base are distilled at 141° C.-144° C. under reduced pressure (typically 0.14-0.15 mbar). The fractions are combined in such a way that the impurity profile of the combined material is within the desired specification.

After distillation, 190 kg AMF base were produced (approximately 67% AMF base distilled).

EXAMPLE 4

Production of Amorolfine HCl and Evaluation of the Purity of the Produced Compound General Considerations:

i) purpose: The aim of this stage is to ensure that sufficient impurities are properly removed with the formation of the Amorolfine HCl and only one crystallization step with ethanol being used.

ii) production of Amorolfine HCl with Amorolfine base (salification step): HCl gas is added to a solution of Amorolfine base in two parts of ethanol until the pH reaches 1.5 to 3. The Amorolfine HCl crystallizes at around 45° C. The slurry is cooled to no less than −15° C. (which should take no less than 2 hours). The crude Amorolfine HCl is isolated by centrifugation and washed with cold ethanol. The crude Amorolfine HCl is then re-crystallized at from −20° to −15° C. from two parts of ethanol.

Schematic of the Process:

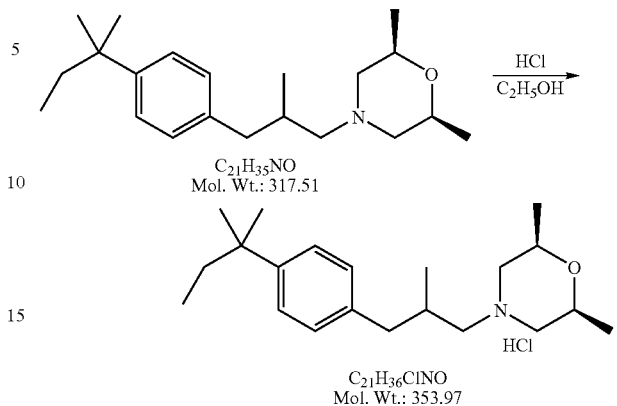

Amounts of by-Products in the Amorolfine Base:

Apart from FPM, all impurities present in AMF base are removed firstly by the salification of AMF base into AMF HCl and secondly by one crystallization step from ethanol.

The data given in Table 3 were taken from different crystallizations experiments.

TABLE 3

|  | Bepromoline (%) | FPM (%) | Trans-isomers (%) |
|---|---|---|---|
| AMF base | 5 | 0.25 | 0.5 |
| AMF HCl crude | 0.3 | 0.25 | 0.3 |
| AMF HCl | <0.1 | 0.25 | <0.2 |
| Required spec. | <0.2 | <0.3 | <0.2 |

Reaction Temperature:

During the addition of the HCl gas, the temperature raises by around 35° C. This exotherm is used to warm the batch. After the addition of HCl the temperature is raised to a level that ensures that the reaction mixture is in solution.

The final temperature of −20° to −15° C. is important to obtain an optimum yield Recrystallization of the Amorolfine HCl:

Ethanol is the preferred solvent. The Amorolfine HCl is dissolved in hot ethanol and this solution is filtered to remove foreign matter. The filtrate is then cooled to −15° to −20° C. to get the optimum yield for crystallization. After centrifugation, the crystals are washed with an appropriate amount of ethanol.

Drying:

The Amorolfine HCl is stable up to 150° C. Drying conditions of 60° C. in a vacuum are used and do not produce any problems with the residual solvent.

b) Synthesis:

(Weights are Given for 1 kmol AMF Base)

The reactor was charged with 317 kg AMF and 640 kg ethanol. 38 kg HCl gas was added at 10°-65° C. The reaction mixture was then heated to 60° C., followed by cooling to −15° to −20° C. The mixture was stored for 30 minutes to 2 hours.

The Amorolfine HCl was centrifuged and washed with 210 kg of ethanol.

2 parts ethanol were used to dissolve the Amorolfine HCl at 70°-80° C.

The hot solution was filtered and the filter rinsed with 15 kg hot ethanol. The filtrate was then cooled to −15 to −20° C. and stored for 30 minutes to 2 hours.

The crystallized Amorolfine HCl was centrifuged and washed with 210 kg of ethanol.

The mixture was then dried at a temperature of 60° C. under vacuum (<100 mbar).

This yielded 271 kg AMF HCl. The yield was approximately 77%

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a compound of formula (I):

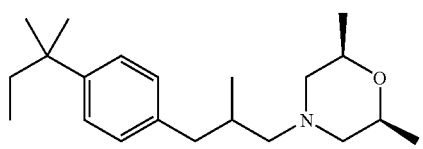

said process comprising the steps of:
(i) contacting a compound of formula (II):

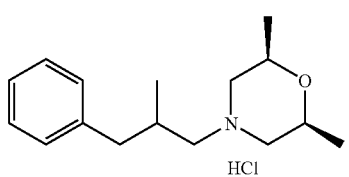

with a Friedel-Crafts catalyst selected from the group consisting of gallium chloride, antimony pentafluoride, molybdenum pentachloride, indium chloride, and antimony pentachloride; and (ii) adding one equivalent of 2-halogeno-2-methylbutane, and wherein the reaction mixture obtained in step (i) is cooled to a temperature from −40° to −60° C. prior to step (ii).

2. The process as defined by claim 1, wherein the reaction mixture obtained in step (i) is cooled to a temperature of −50° C. prior to step (ii).

3. The process as defined by claim 1, wherein the Friedel-Crafts catalyst is selected from the group consisting of gallium chloride, antimony pentachloride and antimony pentafluoride.

4. The process as defined by claim 1, wherein the compound of formula (II) is present in 1 part of 2-halogeno-2-methylbutane per 1 part of the compound of formula (II).

5. The process as defined by claim 1, further comprising one or more of the following steps:
(a) pouring the reaction mixture from step (ii) onto an ice-water mixture;
(b) separating the organic phase;
(c) washing the organic phase with optionally acidified, water,
(d) washing the organic phase with water;
(e) washing the organic phase from step (d) with a solution of sodium hydroxide;
(f) washing the organic phase from step (e) with water;
(g) exchanging the dichloromethane solvent to toluene;
(h) performing toluene/water extractions;
(i) removing the toluene by distillation; and
(j) distilling the crude Amorolfine base from step (i).

6. The process as defined by claim 1, wherein said 2-halogeno-2-methylbutane is 2-chloro-2-methylbutane.

7. The process for producing a compound of formula (V):

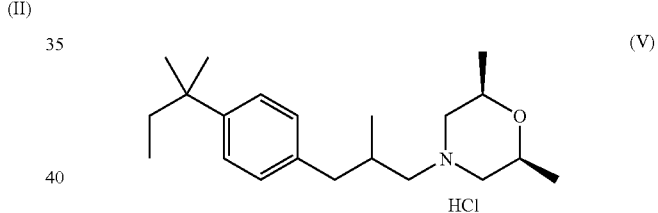

comprising the process as defined by claim 1.

* * * * *